United States Patent
Feldman

(10) Patent No.: US 8,728,136 B2
(45) Date of Patent: May 20, 2014

(54) DEVICE USED FOR TREATMENT OF RHINITIS BY BIOSTIMULATIVE ILLUMINATION

(76) Inventor: Joseph Feldman, Tel Aviv (IL)

( * ) Notice: Subject to any disclaimer, the term of this patent is extended or adjusted under 35 U.S.C. 154(b) by 0 days.

(21) Appl. No.: 13/512,768

(22) PCT Filed: Nov. 25, 2010

(86) PCT No.: PCT/IL2010/000987
§ 371 (c)(1),
(2), (4) Date: May 30, 2012

(87) PCT Pub. No.: WO2011/067752
PCT Pub. Date: Jun. 9, 2011

(65) Prior Publication Data
US 2012/0232618 A1     Sep. 13, 2012

(30) Foreign Application Priority Data
Dec. 2, 2009 (IL) .......................................... 202462

(51) Int. Cl.
*A61N 5/06* (2006.01)
(52) U.S. Cl.
USPC ................................... 607/92; 607/88; 606/14
(58) Field of Classification Search
None
See application file for complete search history.

(56) References Cited

U.S. PATENT DOCUMENTS

| | | | |
|---|---|---|---|
| 5,683,436 A | 11/1997 | Mendes | |
| 2006/0047329 A1 | 3/2006 | Krespi | |
| 2006/0259101 A1* | 11/2006 | Perez | 607/88 |
| 2006/0271024 A1* | 11/2006 | Gertner et al. | 606/2 |
| 2008/0033512 A1* | 2/2008 | Yu | 607/88 |
| 2010/0249763 A1* | 9/2010 | Larson et al. | 606/8 |

FOREIGN PATENT DOCUMENTS

| | | |
|---|---|---|
| DE | 20 2008 011225 | 11/2008 |
| GB | 2445297 | 7/2008 |
| WO | WO 2006/103678 | 10/2006 |

* cited by examiner

*Primary Examiner* — Lynsey Crandall
(74) *Attorney, Agent, or Firm* — The IP Law Firm of Guy Levi, LLC; Guy Levi

(57) ABSTRACT

A device for the treatment of rhinitis by biostimulative illumination. The device comprises a pair of LEDs (504a; 505b) containing probes (202a; 202b) adapted to be inserted into the nostrils of a patient. A probes support casing (204), the probes being normally flexibly attracted one against the other. The casing accommodates an electric power source (502), an ON/OFF normally open micro-switch (504a) and circuit means for activating/deactivating the LEDs (504a; 504b). The casing (204) is made of at least partly elastomeric material whereby the micro-switch (504a) becomes activated by pressing against a side-wing (206a) of the casing also causing the probes to spread apart from each other and the micro-switch remains closed for as long as the probes are kept apart from each other.

6 Claims, 6 Drawing Sheets

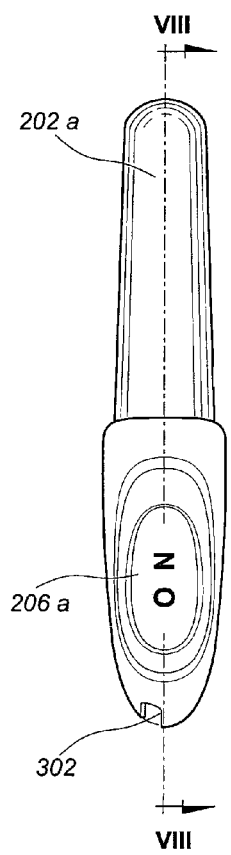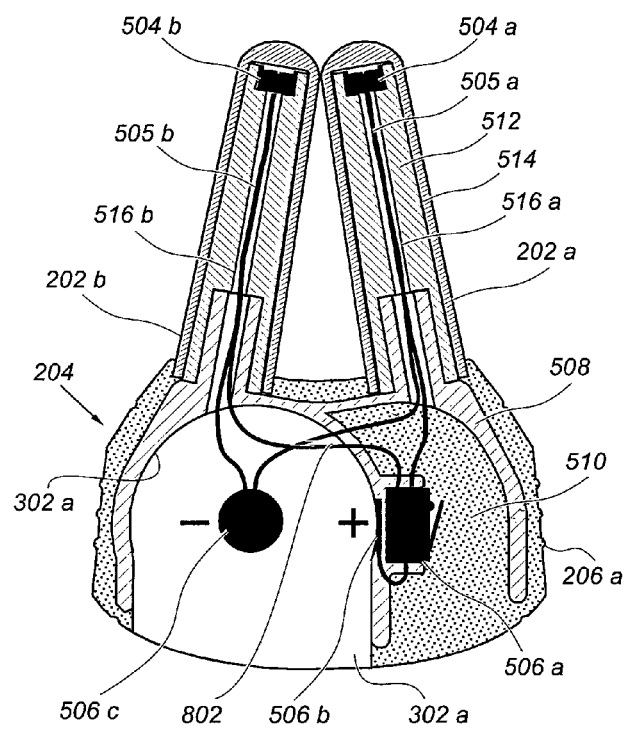
FIG. 7
FIG. 8

DEVICE USED FOR TREATMENT OF RHINITIS BY BIOSTIMULATIVE ILLUMINATION

BACKGROUND OF THE INVENTION

This invention concerns a further development and improvement of apparatus for treating rhinitis, hay fever and the like allergy diseases (hereinafter collectively called "rhinitis") of the type described in U.S. Pat. No. 5,683,436 (Mendes, et al.), which is hereby incorporated by reference (hereinafter referred to as the "Basic Patent").

Briefly stated, the Basic Patent exemplified several options for holding the LEDs (actually the LEDs carrier or casing—hereinafter called the "Probes") within the nostrils of the patient during the treatment periods of time (several minutes daily).

In practice, however, none of these options has been implemented, but rather the design as schematically shown in FIG. 1 of the attached drawings (see for example the site www.syrolight.com under the product "BIONASE"). In more detail, the apparatus comprises a pair of LED or LEDs containing probes 102a and 102b mounted to a common support 104 made of a flexible material such as rubber.

A length of wire 106 with plug 108 leads to the electric power and control housing 110. The housing contains dry or rechargeable batteries and the necessary circuitry for activating the LEDs, along with the conventional auxiliary devices such as pilot lamp 112, on-off switch 114, etc.

Such devices inhibit the release of histamine, relieving or even completely eliminating allergic reactions. There are no side effects associated with the use of the device and there is no need to burden the body with drugs. Therefore, such devices were regarded as an exciting breakthrough for the treatment of allergic reactions.

However, the Bionase-type design certainly involves discomfort on the part of the user, in that it is necessary limits his maneuverability, the same way as experienced with regard to other cord-associated instruments such as Discmans or cellular earphones.

Moreover, this design makes the use by infants and even babies practically prohibitive.

It is thus the prime object of the present invention to overcome the above identified drawbacks of the conventional design.

It is a further object of the invention to make the device cordless-type and thus self-contained.

SUMMARY OF THE INVENTION

There is thus provided, according to embodiments of the present invention, a device for the treatment of rhinitis by biostimulative illumination. The device comprises a pair of LEDs containing probes adapted to be inserted into the nostrils of a patient and a probes support casing which is made of at least partly elastomeric material. The casing accommodates an electric power source, an ON/OFF normally open micro-switch and circuit means for activating/deactivating the LEDs. The micro-switch becomes activated by pressing against a side-wing of the casing which also causes the probes to spread apart from each other.

According to a preferred embodiment of the present invention, the arrangement is such that the micro-switch remains closed for as long as the probes are kept apart from each other.

Furthermore, in accordance with some embodiments of the present invention, the probes are normally flexibly attracted one against the other.

Furthermore, in accordance with some embodiments of the present invention, the casing is made of at least one flexible material.

Furthermore, in accordance with some embodiments of the present invention, the casing comprises a semi-rigid core embedded in a foam elastomeric material.

Furthermore, in accordance with some embodiments of the present invention, the power source comprises a coin-shaped battery which is insertable into a cavity formed in the casing via a slot.

BRIEF DESCRIPTION OF THE DRAWINGS

These and additional constructional features and advantages of the invention will be more readily understood in the light of the ensuing description of some preferred embodiments thereof, given by way of example only, with reference to the accompanying drawings wherein:

FIG. 7 is again a schematic side-view of the device of FIG. 2;

FIG. 8 is a schematic cross-sectional view of the device taken along the VIII-VIII line of FIG. 7 but with the battery removed;

DETAILED DESCRIPTION OF THE PREFERRED EMBODIMENTS

Figure 1:
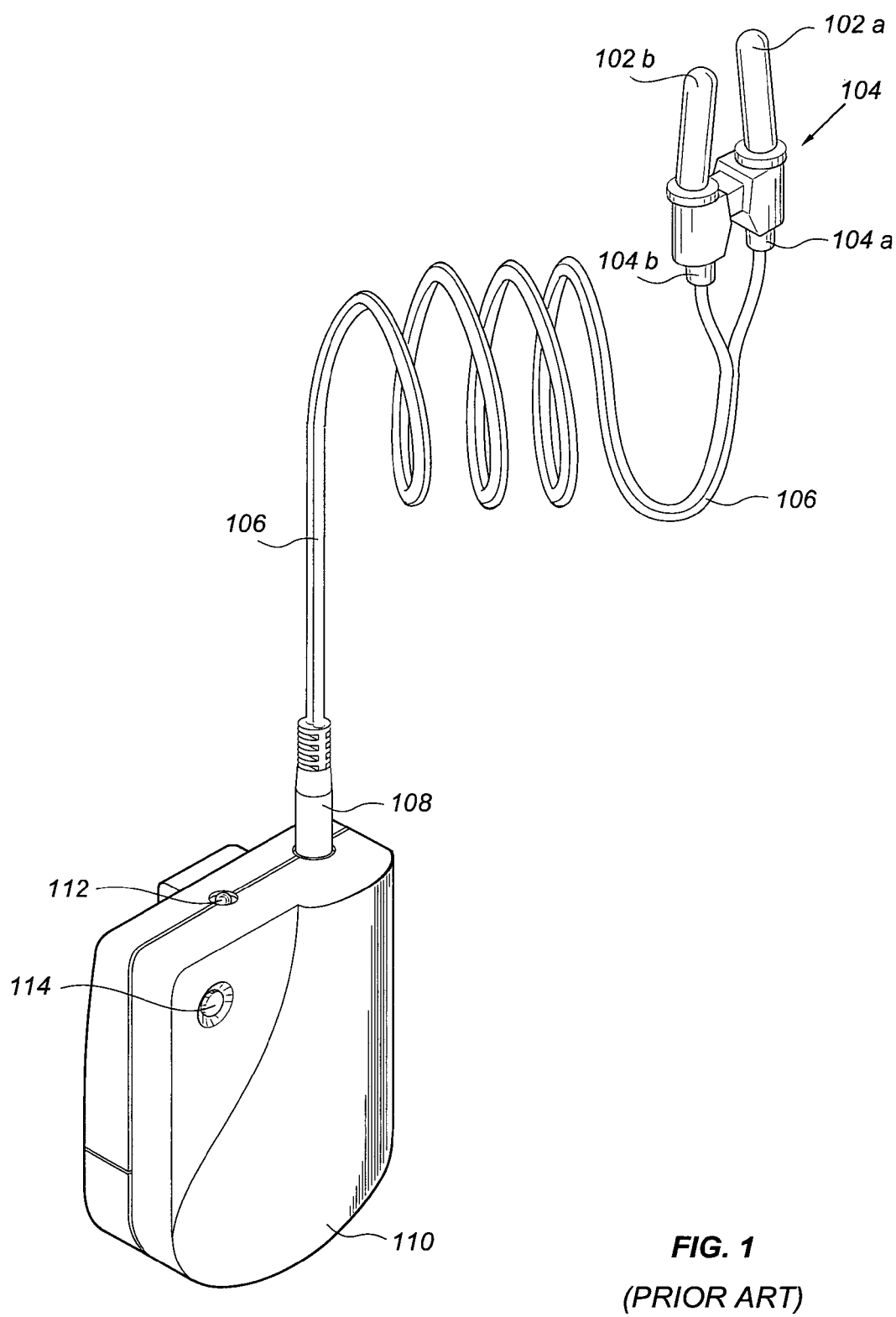
FIG. 1 illustrates a typical prior art apparatus.
Figure 2:
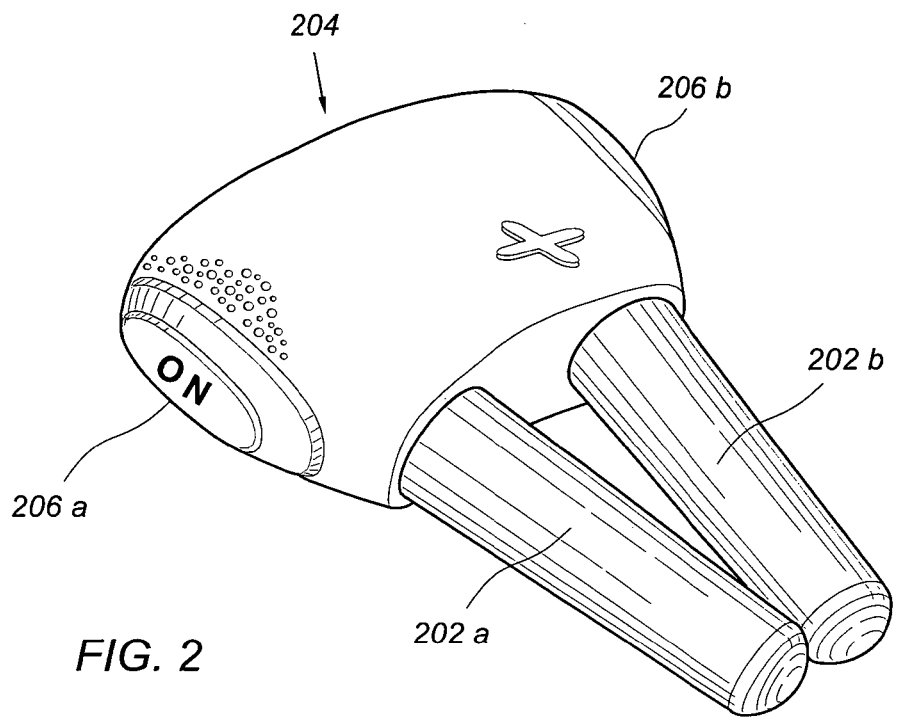
FIG. 2 is a schematic top perspective-view of the device according to a preferred embodiment of the present invention.
Figure 3:
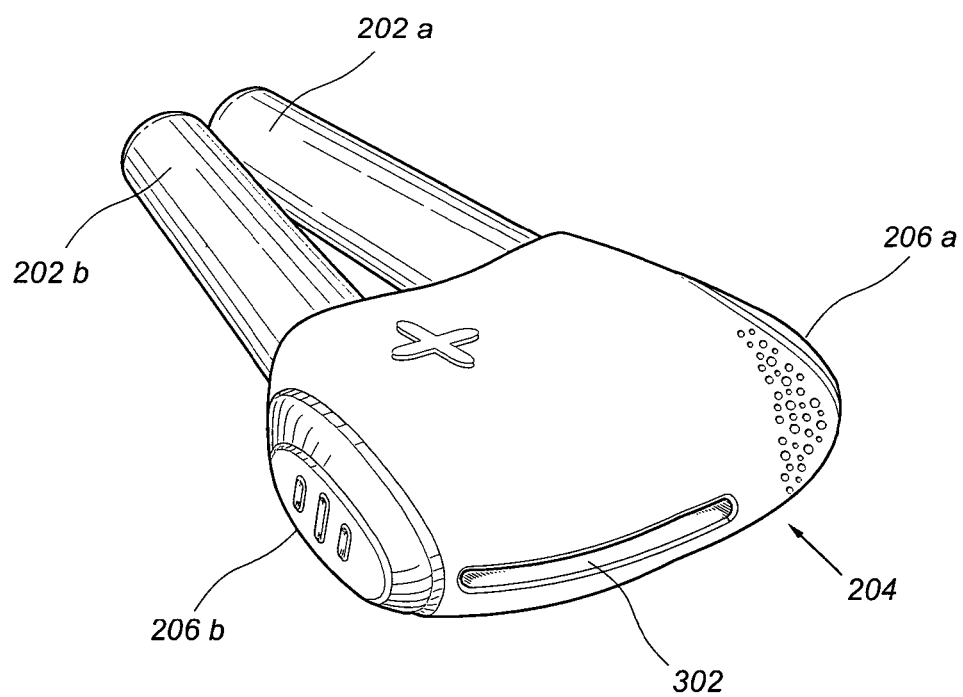
FIG. 3 is a schematic bottom perspective-view of the device of FIG. 2.

Referring to FIGS. 2 and 3, the device according to a preferred embodiment of the present invention is designed in such a way that the probes and the associated control parts and components are integrated into a single-piece, generally pillow-shaped package, resulting in a self-contained device. Thus, probes 202a and 202b are mounted on casing 204 which encloses the entire circuitry of the device. Casing 204 may be made of flexible-type materials such as, for instance, elastomers, and the like as will be described in greater detail below.

In a standby position, the probes are tilted towards one another as shown in the figures. However, prior to use, e.g., prior to inserting the probes into the nostrils, pushing against two opposite side-wings 206a and 206b causes probe 202a and probe 202b to elastically spread apart to facilitate the insertion of the probes into the nostrils as well as to activate the electrical circuit as will be described in detail further below.

Seen in FIG. 3 is a slot 302 through which the power source, preferably a coin-type battery, slides into a cavity 302a formed within casing 204 (see FIG. 8).

Figures 4, 5:
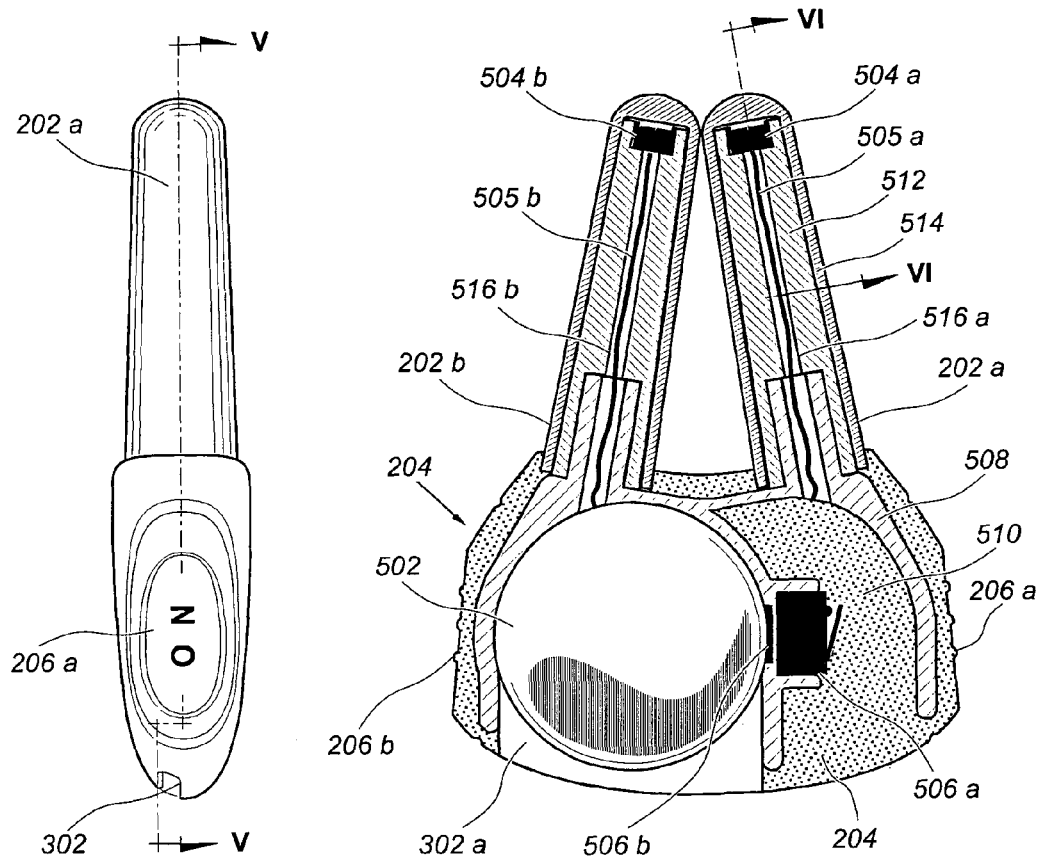
FIG. 4 is a schematic side-view of the device of FIG. 2.
FIG. 5 is a schematic cross-sectional view of the device taken along the V-V line of FIG. 4.

FIG. 4 clearly shows the region to be pushed, namely side-wing 206a in order to cause probe 202a to spread apart from probe 202b (not shown in this figure). Also seen here is a side-view of slot 302 through which the battery slides into position.

Seen in FIG. 5 are the inner components of the device, which include coin-type battery 502, LEDs 504a and 504b, wires 505a and 505b leading thereto, contact 506b, and normally open micro-switch 506a. Also seen in FIG. 5 is the basic structure of the device. The device, according to some embodiments of the present invention, may be made of at least two different materials selected from rigid, semi-rigid, and flexible-type materials such as, for instance, polymeric materials of various types. Using material combinations as such enables the fabrication of a cordless-type, compact and portable device.

Thus, according to some embodiments of the present invention, casing 204 contains reinforcing skeleton or core 508 that is made of a semi-rigid type material such as for instance semi-rigid type polymers. The core 508 is embedded in filling material 510 which may be a foam or a composite of foams made of elastomeric materials. Probes 202a and 202b are structured to include at least two layers, i.e., inner sleeve 512 which is made of a flexible-type material such as elastomers, and a capped sheath 514 which may be made either of a semi-rigid or a rigid plastic material.

Figure 6:
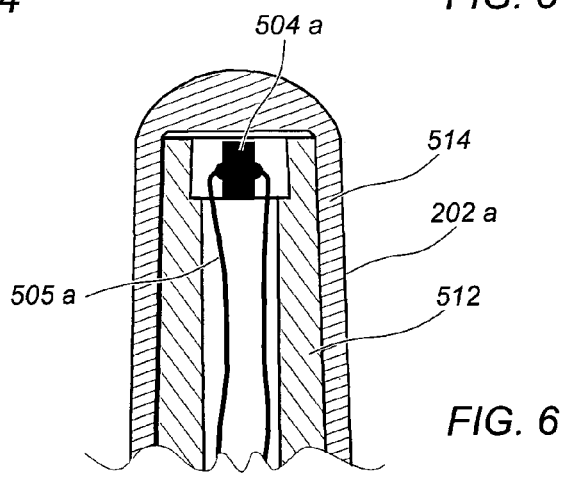
FIG. 6 is a magnified cross-sectional view taken along line VI-VI of FIG. 5.
Figure 9:
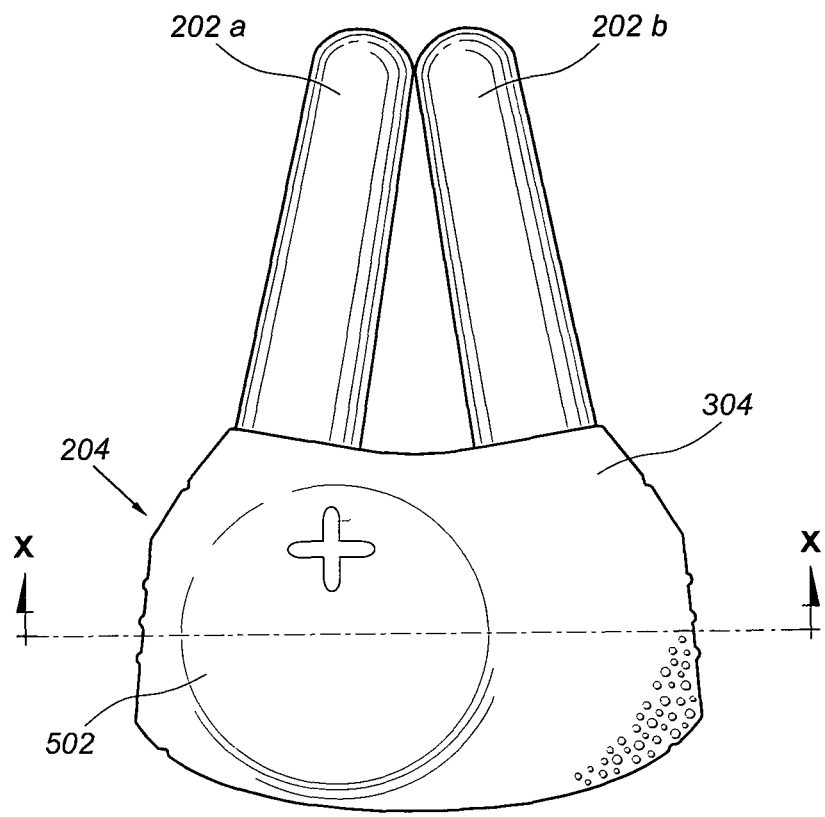
FIG. 9 is a schematic bottom view of the device of FIG. 2.

Sleeves 512 are formed with passages 516a and 516b within which LEDs 504a and 504b and wires 505a and 505b are accommodated as better seen in FIG. 6.

It should be noted that the specific configuration of 508 and the use of a foamy-type filling material 504 is an essential combination of the present design since it allows for spreading the probes as desired (see FIG. 11) and thus allows the fabrication of such compact and easy for use device.

Figure 11:
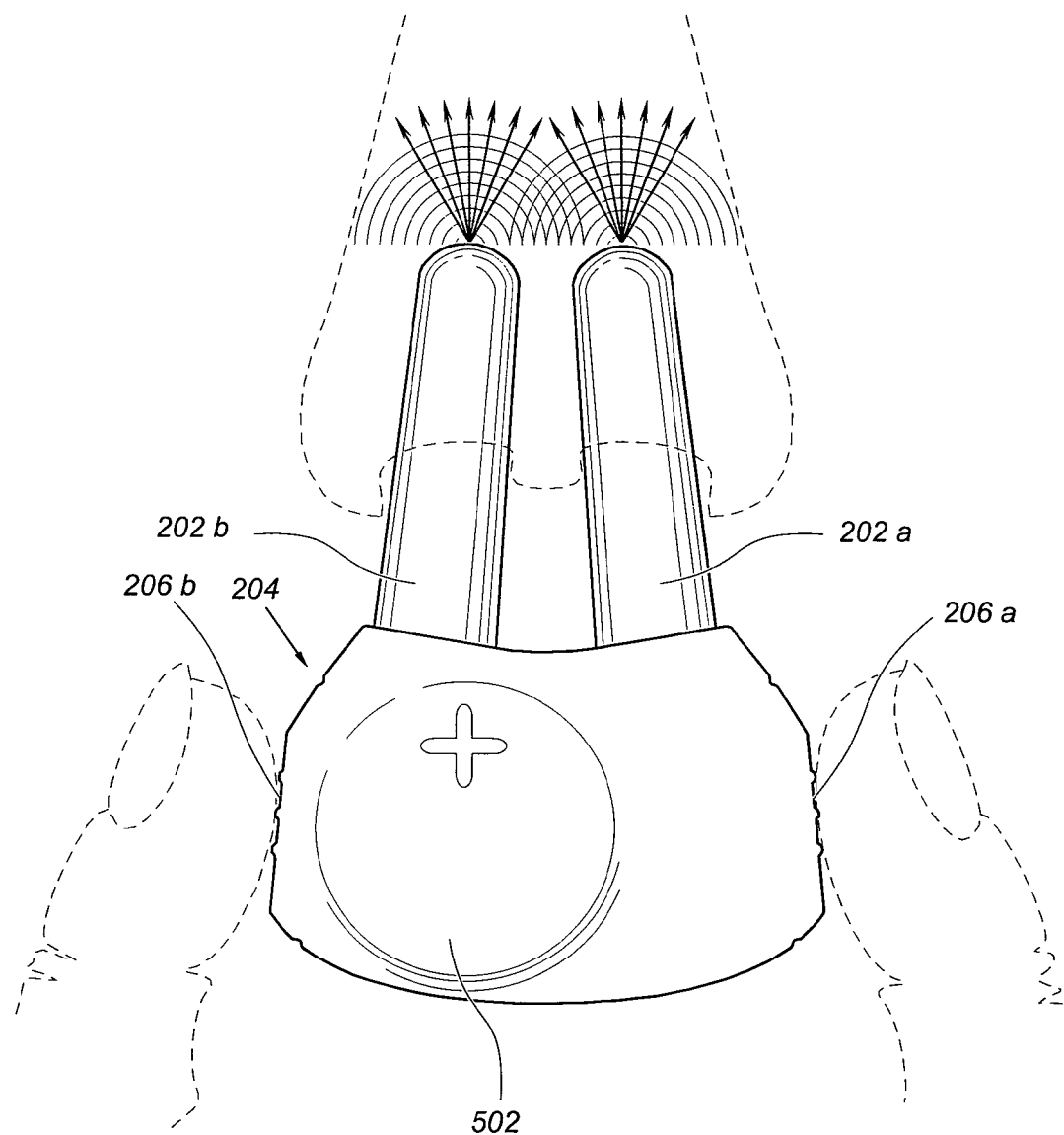
FIG. 11 illustrates the mode of use of the device.

A further unique feature of the device is that the very spreading apart of the probes also causes the actuation of micro switch 506a. This is achieved by pushing side-wing 206a (marked "ON" in FIG. 4) thereby compacting the elastomeric material 510 for transferring the pressure to the switching component of the micro switch (see FIG. 5). The switch 506a will be kept closed for as long as the pressure remains, namely the probes being held distanced from each other as in case inserted into the nostrils of the patient (FIG. 11).

Additional details of the interior structure and circuitry are seen FIG. 8.

Contact 506b constantly engages the (+) pole, and contact 506c constantly engages the (−) pole of the coin-type battery 502 when inserted into cavity 302a.

Figure 10:
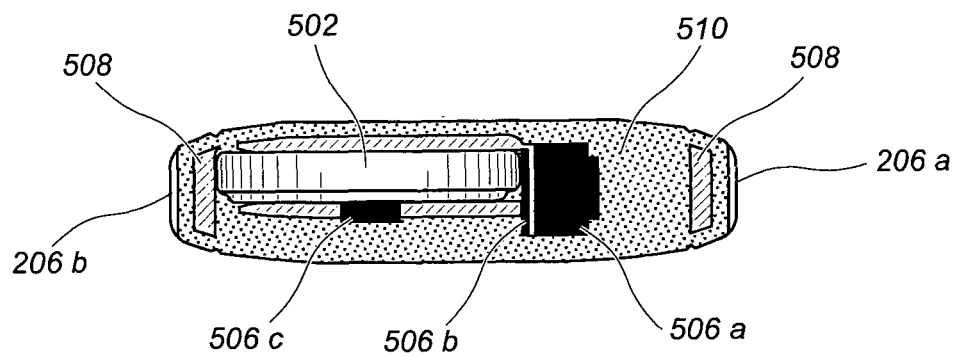
FIG. 10 is a schematic cross sectional top-view of the device taken along the X-X line of FIG. 9 according to a preferred embodiment of the present invention.

It should be noted that the device can be readily fabricated in a single manufacturing process such as, for instance, an injection molding process to form a unified structure. Thus, skeleton 508, LEDs 504a and 504b, wires 505a and 505b, contacts 506b, 506c and switch 506a are all injection molded into a unitary implement in a single-step operation by one production process as exemplified in FIG. 10.

As vividly seen in FIG. 11, by clamping casing 204 from side wings 206a and 206b thereof, the probes spread apart against the elasticity of the composite inner structure (core 508 and filling 510), thereby activating switch 506a to close the electric circuit.

It should be noted that the battery should have a high enough capacity to allow multiple session treatments (typically 3 minutes long) before replacement (typically after 4 hours of continuous use).

Thus established is that a self-contained, cordless-type device as described above frees the patient from being "wired" during treatment. Therefore, the patient may feel much more comfortable during the treatment sessions. Moreover, such cordless device would be highly recommended for treating small children as there are no cords by which children can get strangled, and the device can be made in various sizes to fit children or adults.

Those skilled in the art to which this invention pertains will readily appreciate that numerous changes, variations and modifications can be effectuated without departing from the true scope of the invention as defined in and by the appended claims. Thus, for instance, the operating side-wing 206a may be separate, hinged to the casing and spring-urged, rather than the casing being filled with the foam elastomaric material 510; the LEDs activation circuit may comprise a timer for presetting the duration of the treatment session; a battery capacity indicator; etc.

What is claimed is:

1. A device for the treatment of rhinitis by biostimulative illumination comprising:
   a pair of LEDs containing probes adapted to be inserted into the nostrils of a patient, said probes being biased towards each-other; and
   a housing, said housing accommodating an electric power source, an ON/OFF, micro-switch in the open position at default, and circuit means for activating/deactivating the LEDs, the housing further comprising:
   (a) a first and a second, opposite, side-wings;
   (b) the first side-wing being integrally formed with the housing; and
   (c) the second side-wing being flexibly mounted to the housing, wherein, said second side wing, when pressed, causes both spreading apart of the probes and activation of the micro switch.

2. The device as claimed in claim 1 wherein the micro-switch is maintained activated for as long as the probes are kept apart from each other.

3. The device as claimed in claim 1, wherein said housing is made of at least one flexible material.

4. The device as claimed in claim 3, wherein the housing comprises a semi-rigid core embedded in a foam elastomeric material.

5. The device as claimed in claim 1, wherein said power source comprises a coin-shaped battery.

6. The device as claimed in claim 5, wherein said coin-shaped battery is insertable into a cavity formed in the housing.

* * * * *